United States Patent [19]

Shaw, Jr.

[11] Patent Number: 4,538,912
[45] Date of Patent: Sep. 3, 1985

[54] METHOD OF AND APPARATUS FOR INSPECTION OF COATINGS ON SURFACES

[75] Inventor: Hugh E. Shaw, Jr., Crystal City, Mo.

[73] Assignee: PPG Industries, Inc., Pittsburgh, Pa.

[21] Appl. No.: 426,385

[22] Filed: Sep. 29, 1982

[51] Int. Cl.$^3$ ............................................. G01N 21/21
[52] U.S. Cl. .................................. 356/366; 356/369; 356/237
[58] Field of Search ............... 356/366, 369, 445, 448, 356/237, 351, 357

[56] References Cited

U.S. PATENT DOCUMENTS

| | | | |
|---|---|---|---|
| 2,947,212 | 8/1960 | Woods | 88/14 |
| 3,028,783 | 4/1962 | Peters | 88/14 |
| 3,355,980 | 12/1967 | Mathias | 88/14 |
| 3,395,278 | 7/1968 | McDivitt | 250/83.3 |
| 3,609,045 | 9/1971 | Stein | 356/448 X |
| 3,612,692 | 10/1971 | Kruppa et al. | 356/351 X |
| 3,773,420 | 11/1973 | Conroy | 356/51 |
| 3,857,637 | 12/1974 | Obenreder | 356/120 |
| 3,871,773 | 3/1975 | Shaw, Jr. | 356/200 |
| 3,994,586 | 11/1976 | Sharkins et al. | 356/445 X |
| 4,015,127 | 3/1977 | Sharkins | 356/369 X |
| 4,017,188 | 4/1977 | Sawatari | 356/120 |

FOREIGN PATENT DOCUMENTS 43039 12/1966 Japan ...................... 356/369

OTHER PUBLICATIONS

Andrews, *Optics of the Electromagnetic Spectrum*, Prentice-Hall, Inc., Englewood Cliffs, NJ, pp. 392–396, 1960.
Bishop, Jr., "Surface Layer of Sheet Glass", *J. Am. Ceram. Soc.*, vol. 27, No. 5, pp. 145–148, May 1944.

Primary Examiner—Davis L. Willis
Assistant Examiner—Matthew W. Koren
Attorney, Agent, or Firm—Robert A. Westerlund, Jr.; Donald Carl Lepiane

[57] ABSTRACT

A method of and apparatus for inspecting reflective coatings on a substrate using a polaroid filter to view light reflected from the coating to make variations in coating thickness over a large coated area visible.

9 Claims, 1 Drawing Figure

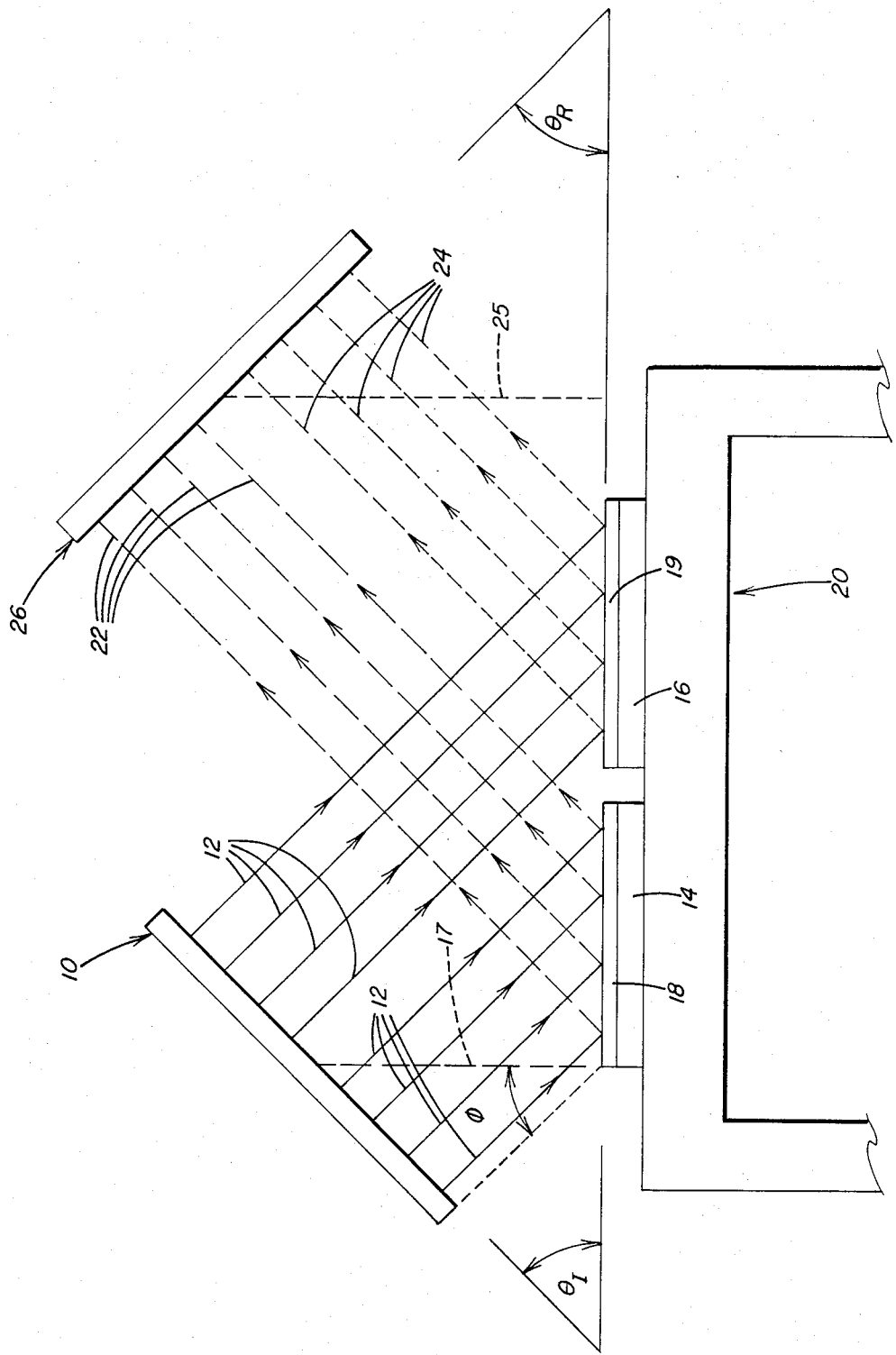

METHOD OF AND APPARATUS FOR INSPECTION OF COATINGS ON SURFACES

BACKGROUND OF THE INVENTION

1. Field of the Invention

This invention relates to a method of and apparatus for inspecting coatings on a substrate, particularly reflective coatings on a flat glass substrate.

2. Discussion of the Presently Available Techniques

Developments in the glass coating art and in particular, in the area of architectural glass, have led to a variety of techniques for depositing thin reflective coatings on a glass substrate. Both discrete glass sheets and a moving glass ribbon have been coated to provide the desired reflectivity, as well as aesthetically pleasing color. For example, U.S. Pat. No. 3,660,061 teaches a method of applying a pyrolytic coating to a moving glass ribbon, and Canadian Pat. No. 756,053 teaches a method of coating discrete glass sheets.

As can be appreciated, any coating must be uniformly applied to a moving ribbon so that discrete sheets cut from the ribbon will have a consistently uniform appearance when installed side by side, e.g. in a curtainwall construction. Individual sheets as well must be free from visible color variations and defects. For this reason, uniform thickness of the coating is important to achieve the desired uniform appearance. Variations in coating thickness which appear as color and shading variations in the installed sheet are not readily visible to the naked eye observing either the moving coated ribbon, or the sheets cut from the ribbon, under normal ambient lighting conditions in the production facility. For this reason, some inspection technique is necessary to assure the quality of the coated glass with respect to uniformity of coating thickness.

One technique available for the inspection of such coatings on the production line includes a device such as that sold under the trade name of Chromoscope by the Millitron Company of Pittsburgh, Pa. This device is mounted in a stationary position above a moving ribbon of coated glass and incident light is directed at a selected angle to a point on the coated surface. Light reflected from the point on the surface is received by the device which measures the reflectance of blue light and the reflectance of red light and determines the thickness of the film as a function of the ratio of these measured reflectances. The flow rate of the filming composition is then adjusted, if necessary, to compensate for any variation from desired thickness.

U.S. Pat. No. 3,395,278 teaches a method of measuring the thickness of a transparent metallic oxide coating on articles by using an ultraviolet light source and measuring the degree of reflectivity of light from a single point on the coating, and converting the degree of measured reflectivity into a reading of coating thickness.

Although it might be possible to adapt either of these methods for scanning the entire surface of a moving ribbon, because of their inherent limitations, this is impractical. This is so because both methods as practiced operate on a beam reflected from the single point on the coated surface. As can be appreciated, providing facilities for scanning the entire surface in a pointwise fashion is slow, and the apparatus for accomplishing the task would be complex and costly.

Another method used to inspect coatings on glass panels is to visually inspect a sample of the coated glass outdoors under natural sunlight conditions. Generally, this method is used in addition to an online reflectance ratio monitoring device similar to the type discussed above, and it is used to detect variations which may have escaped detection by the online device, but would appear as color variations in a coated glass panel after installation. This technique is primarily used to detect the defect known as "banding", which is the term used for variations in coating thickness which consist of alternating fairly wide bands of thick and thin coating. Although this method allows visual inspection of an entire sample surface and can reveal banding, it has limitations. For example, this technique cannot be used for online inspection and furthermore, samples are not easily inspected on cloudy or dark days.

As can now be appreciated, it is desirable to have a simple, fast method of inspecting coating thickness on a substrate, e.g. a glass panel, that does not have the limitations of the presently available techniques.

SUMMARY OF THE INVENTION

This invention relates to a method of inspecting coatings on a substrate, e.g. a glass substrate, to detect variations in the coating. Energy beams, e.g., light beams, are directed toward the coating to be inspected and reflected from the coating as reflected energy beams. The reflected beams are incident on an analyzer which vertically polarizes the reflected light beams. The polarized light passing through the analyzer is acted on to detect variations in the coating. When the reflected beams are viewed through the analyzer, e.g. an analyzer, variations in coating thickness appear as variations in color and shading on the coated surface. In this manner, banding, fingerprints, and other similar defects in the coating thickness which affect the quality of the coated glass are discernible.

This invention also relates to an apparatus for inspecting coatings on a substrate which includes a source of energy beams, e.g. a light source, facilities for directing beams toward the coatings to ve inspected to reflect beams from the coating, and facilities for intercepting the reflected beams to vertically polarize the reflected light beams.

By practicing the instant invention, a human observer can quickly scan an entire coated surface for undesirable variations in coating thickness under artificial lighting conditions at any time.

BRIEF DESCRIPTION OF THE DRAWING

The FIGURE is an elevated side view of an apparatus incorporating features of the invention for viewing thickness variations in a coating on a substrate.

DESCRIPTION OF A PREFERRED EMBODIMENT

While the present invention wil be described in terms of a method and apparatus for inspecting pyrolytic coatings on a glass substrate, it is understood that the invention is not limited thereto and may be used to inspect any type of reflective coating deposited on a substrate.

As shown in the drawing, an energy source 10, e.g. a diffused light source, directs energy beams 12, e.g. light beams, toward a coated sample 14 to be inspected, and a standard coated sample or reference sample 16. The light is directed toward the samples at an angle of incidence $\phi$, i.e. the angle subtended by a line 17 normal to a sample coating 18 or a reference coating 19 and the path of the incident beams 12. Although not limiting to the invention, the sample 14 and the standard 16 may be conveniently supported by a table 20 as shown in the drawing.

The reference sample 16 may conveniently be selected by using known laboratory spectroscopy techniques to preselect a coated sample which meets desired quality control standards. In this manner, the quality of the coating 18 on the sample 14 can be compared to the coating 19 on the reference sample 16 by viewing both simultaneously through analyzer 26, as discussed below.

The light beams 12 incident on the sample coating 18 are reflected therefrom as sample reflected energy beams 22, e.g. sample reflected light beams, and from the reference coating 19 as reference reflected energy beams 24, e.g., reference reflected light beams. The sample coating 18 and the reference coating 19 are viewed through the analyzer 26 which selectively passes portions of the beams 22 and 24 in the manner discussed below, to determine variations in the coating thickness. The reflected beams 22 and 24 are reflected at an angle $\theta_R$ which is substantially equal to the angle of incidence $\theta_I$ according to well known optical principles.

The analyzer 26 is preferably selected to vertically polarize light. Although not limiting to the invention, types of analyzers that may be used in the practice of the invention include an analyzer, nichol prism, or other dichroic crystal.

Nonuniformity of the coating thickness on a given sample is visible as lighter and darker areas and lines on the surface revealing a pattern corresponding to variations in coating thickness. It has been observed that relatively light blue areas on the pyrolytic coating such as is taught in U.S. Pat. No. 3,660,061, indicate a relatively thick coating, and darker blue or violet areas indicate a relatively thin coating. In addition, fingerprints can be seen as a recognizable pattern of dark lines and light areas.

As can now be appreciated, although use of the reference sample is not limiting to the invention, it is a convenient method of determining whether an inspected sample meets predetermined desired quality control standards. The reference sample 16 can be selected by analyzing production line coated glass samples using known laboratory spectroscopy techniques to select a sample representing a coating of minimum acceptable commerical quality with regard to minimum coating thickness and maximum variations in thickness, e.g. banding. The reference sample can be conveniently compared to the sample to be inspected using the invention to view both samples simultaneously. In this manner, if the inspected sample 14 appears darker overall than the reference sample 16, the coating is too thin and if the shading across the sample varies more than on the reference sample, it is of unacceptable quality with respect to coating uniformity.

It was found that these variations in coating thickness are also visible, although with a somewhat lower optical resolution, when the analyzer is placed in the path of the incident beams 12. Furthermore, placing an analyzer in the paths both of the incident beams 12 and the reflected beams 22 and 24 produces results only slightly better than when the analyzer is in the reflected beam only. Although it is not completely understood, it is believed that the combined phenomena of polarization of light and of destructive and constructive interference of selected wavelengths of light by the coating produce the distinctive pattern observed on the coating surface when light reflected from the samples is viewed through an analyzer.

Although the exact spacial relationship of the elements of this invention is not crucial to its practice, the following particular embodiment is given to illustrate the practice of the invention for inspecting coated samples of relatively large dimension.

The invention was used to inspect samples cut from a glass ribbon which was pyrolytically coated in the manner described in U.S. Pat. No. 3,660,061, the teachings of which are hereby incorporated by reference. A bank of 32 full spectrum tubular flourescent lights, each approximately 4 feet (1.2 m) in lenght, type F40TI12VLX Full Spectrum, manufactured and sold by Verilux, Inc. of Greenwich, Connecticut, were used in conjunction with a diffuser panel to provide a diffused light source 10 (shown as rectangular box 10 in the drawng) approximately 4 feet×8 feet (1.2 m×2.4 m) in area. Although not limiting to the invention, full spectrum lights were used to enhance the blue hue in the reflected analyzed beams in order that the variations in coating thickness could be more readily discerned as differences in intensity of the blue color seen through the analyzer. A 40 inch by 40 inch (101.6 cm×101.6 cm) reference sample 16, and a similarly sized sample 14 to be inspected, were placed on the table 20. The light source 10 and table 20 were positioned such that the angle $\theta_I$ subtended by the plane of the light and plane of the table surface was approximately 75°, and the distance between the light source and the table measured along normal 17 from the center of the source 10 to the table surface was approximately 3½ feet (1.1 m). An analyzer 26 approximately 30 inches by 36 inches, of the type manufactured and sold by Polaroid Corporation, under their registered trademark polaroid ®, was positioned in the path of the reflected beams 22 and 24 such that the angle $\theta_I$ subtended by the plane of the filter and that of the table surface was also approximately 75°, and at an elevantion of about 3½ feet (1.1 m) from the table measured along normal 25. An observer stood in a convenient position behind the filter, i.e. to the right of the filter 26, as shown in the drawing, and was thus able to observe the reflected light beams 22 and 24 as polarized light. As can be appreciated, with a large area an analyzer, the observer can move his head to view the entire surface of both samples 14 and 16 to search for areas in the sample 14 which appear darker or lighter in hue than the hue of the reference sample 16. Alternatively, the observer may hold an analyzer in his line of sight and move his head together with the filter to scan the entire surface of the samples 14 and 16.

As practiced to inspect pyrolytic coatings, thicker coatings appear to the observer as light blue areas on the sample, while thinner coatings are a darker shade of blue with a slight purple cast. Banding is visible as alternate light and dark areas and fingerprints appear as alternate light and dark blue lines. It was found that variations in the coating thickness appeared as a recognizable pattern on the coated glass when the angles $\theta_I$ and $\theta_R$ were in the range from about 20° to about 80°, although best resolution was obtained at approximately 75°. With this arrangement, variations in the coating could be readily discerned by the human inspector.

As can now be appreciated by those skilled in the art, the image viewed through the analyzer may be sharpened by using a collimated light source, e.g. a point source and concave mirror and/or collimating lens, as opposed to the diffused source described above. In addition facilities for focusing the reflected light beams may be added, and the focused image recorded on a photographic emulsion for later comparison, if desired. Further additions to the optical system, as will readily occur to one skilled in the art, can be made depending upon the sensitivity desired and the dimensions of the coated surface to be inspected.

The method and apparatus of the invention can be used to inspect large coated surfaces over their entire surface in a very short time, and the inspection can be accomplished indoors, at any time, and in any convenient location. It is understood various changes other than those mentioned above may be made without departing from the spirit of the invention as defined in the claimed subject matter that follows.

What is claimed is:

1. A method for inspecting coatings on a substrate, comprising the steps of:
   generating energy beams;
   directing said beams toward both a sample coated substrate and at least one reference coated substrate to reflect beams therefrom as sample reflected beams and reference reflected beams respectively;
   positioning an analyzer in the paths of both said sample reflected beams and said reference reflected beams to polarize said sample reflected beams and said reference reflected beams; and
   comparing said polarized sample reflected beams and said polarized reference reflected beams to compare color variations on the sample coating and on the reference coating.

2. The method as set forth in claim 1 wherein said directing step includes directing said beams at an angle of incidence of between 20° an 80°.

3. The method as set forth in claim 2, wherein said angle of incidence is close to 75 degrees.

4. The method as set forth in claim 1, wherein said responding step includes visually comparing said polarized sample reflected beams and said polarized reference reflected beams through said analyzer.

5. The method as set forth in claim 4, wherein said at least one reference coated substrate is selected to represent a coating or predetermined minimum acceptable quality regard to minimum coating thickness and maximum variations in thickness.

6. The method as set forth in claim 5, wherein said at least one reference coated substrate is selected by analyzing coated glass substrates using spectroscopic means to select a sample representng a coating of predetermined minimum acceptable quality with regard to minimum coating thickness and maximum variations of thickness, and wherein further, if the substrate under inspection appears darker overall, through said analyzer, than said reference coated substrate, then the substrate coating is too thin, and if the shading across the substrate varies more than on said reference coated substrate, it is of unacceptable quality with respect to coating uniformity.

7. A method for inspecting coatings on a substrate, comprising the steps of:
   generating energy beams;
   directing said beams toward at least one coated substrate to reflect said beams therefrom as reflected energy beams;
   positioning an analyzer in the path of said reflected energy beams to polarize said reflected energy beams; and
   visually observing said analyzer to detect color variations in the coating on the substrate.

8. The method as set forth in claim 7, wherein said analyzer positioning step includes positioning said analyzer in the path of the reflected beams to vertically polarize said reflected beams.

9. Apparatus for inspecting coatings on a substrate, comprising:
   a light source for generating light beams;
   means for directing said beams toward the coating to be inspected to provide reflected energy beams including at least a portion reflected from the upper surface of the coating;
   means for vertically polarizing said reflected light beams to provide polarized reflected beams; and
   means for recording image or shading pattern produced on said polarizing means by said reflected light beams passing therethrough.

* * * * *